(12) United States Patent
Traudt

(10) Patent No.: US 7,559,226 B2
(45) Date of Patent: Jul. 14, 2009

(54) RADIANT THERMAL ENERGY ABSORBING ANALYTICAL COLUMN

(75) Inventor: Sammye E. Traudt, Middletown, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 134 days.

(21) Appl. No.: 11/434,963

(22) Filed: May 16, 2006

(65) Prior Publication Data

US 2007/0266767 A1 Nov. 22, 2007

(51) Int. Cl.
*G01N 30/60* (2006.01)

(52) U.S. Cl. .............................. 73/23.39; 95/87; 96/101; 422/89

(58) Field of Classification Search ................. 73/23.35, 73/23.39; 95/82, 87; 96/101; 422/89
See application file for complete search history.

(56) References Cited

U.S. PATENT DOCUMENTS

| | | | | |
|---|---|---|---|---|
| 4,359,323 A | * | 11/1982 | LePage | ..................... 436/89 |
| 5,036,179 A | * | 7/1991 | Westerberg et al. | .......... 219/411 |
| 5,262,031 A | * | 11/1993 | Lux et al. | .................... 204/601 |
| 5,736,036 A | * | 4/1998 | Upchurch et al. | ........ 210/198.2 |
| 5,808,178 A | | 9/1998 | Roundbehler et al. | |
| 5,837,883 A | * | 11/1998 | Itoi | ........................... 73/23.37 |
| 5,939,614 A | | 8/1999 | Walters et al. | |
| 5,979,221 A | * | 11/1999 | Walte et al. | ................. 73/23.25 |
| 6,186,850 B1 | * | 2/2001 | Cathey et al. | .................. 445/24 |
| 6,316,759 B2 | | 11/2001 | Gaisford et al. | |
| 6,783,673 B2 | * | 8/2004 | Horsman et al. | ......... 210/198.2 |
| 2001/0041151 A1 | * | 11/2001 | Gorecki et al. | ................ 422/89 |
| 2006/0239665 A1 | * | 10/2006 | Miller | ........................ 392/416 |

FOREIGN PATENT DOCUMENTS

SU 1654798 A1 * 6/1991

OTHER PUBLICATIONS

"Frequently Asked Questions: Halogen Lamp Ultraviolet Output—Do Tungsten Halogen Lamps Emit Ultraviolet Radiation ?" Osram Sylvania, 2000, p. 1.*

* cited by examiner

*Primary Examiner*—Daniel S Larkin (57) ABSTRACT

An analytical column includes a coating that absorbs at least one of ultraviolet (UV) and visible (VIS) radiant energy and converts the radiant energy into heat.

14 Claims, 6 Drawing Sheets

RADIANT THERMAL ENERGY ABSORBING ANALYTICAL COLUMN

BACKGROUND

Many chemical separation analyses, such as gas and liquid chromatography, require the chemical sample to be temperature-controlled throughout the analysis. A chromatograph comprises an inlet where the sample is introduced, an oven containing an analytical column where the separation takes place, and a detector where the constituents of the sample are detected and recorded. Each of these parts of the instrument is temperature-controlled to ensure the integrity and repeatability of the analysis. An analysis performed at a constant controlled temperature is referred to as isothermal. To perform an isothermal analysis, the analytical column is typically placed in a temperature-controlled chamber, often referred to as an oven that is preheated to the desired temperature. A non-isothermal analysis, in which the column temperature is gradually raised over time, is also common, especially for samples with relatively massive components that would otherwise take a long time to elute from the column.

Conventional chromatographic ovens typically use convection technology to heat and maintain the interior of the chamber, and hence the analytical column, at the desired temperature. However, conventional ovens are relatively large in comparison to an analytical column which they are intended to heat and, as a result, are very power inefficient. In addition to cost, a side effect of power inefficiency is that the oven is slow to heat and cool, resulting in reduced sample throughput and productivity.

One prior solution to reduce power consumption when heating an analytical column is to use a resistively heated analytical column. Unfortunately, this technology requires a specially fabricated column that may be incompatible with existing chromatography systems. In addition, an analytical column is susceptible to contamination at its input usually due to sample build-up over time. The contaminated portion of the analytical column is typically removed so the column can be reused. This is difficult or impossible to do when using a resistively heated column since the column and heating element are bundled together. Further, it is difficult to precisely determine the temperature of a resistively heated analytical column because it is difficult to place a temperature probe so that its temperature tracks the temperature of the resistively heated column precisely.

Another prior solution to heat a chromatographic column is to use a microwave energy source to heat a chromatographic column that is coated with a microwave energy absorbing material. Unfortunately, microwave heating often results in uneven heating of the column. Also, as with the resistively heated analytical column, determining the precise temperature of an analytical column heated by a microwave source is difficult because it is difficult to ensure that a temperature probe absorbs and converts the microwave energy to heat in the same way as the column to provide an accurate measure of the column temperature. Finally, the directional or "line-of-sight" nature of an EM radiant source adds a potential source of temperature gradients across the column that would not be present in a conventional convection oven.

Therefore, it would be desirable to efficiently heat a chromatographic column and accurately determine its temperature.

SUMMARY OF INVENTION

According to one embodiment, an analytical column comprises a coating that absorbs at least one of ultraviolet (UV) and visible (VIS) radiant energy and converts the radiant energy into heat. The heat is transferred directly to the analytical column.

Other embodiments and methods of the invention will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures.

DETAILED DESCRIPTION

While described below for use in a gas chromatograph, the analytical column to be described below can be used in any analysis application where it is desirable to quickly and efficiently heat and cool an analytical column or other device.

Figure 1:
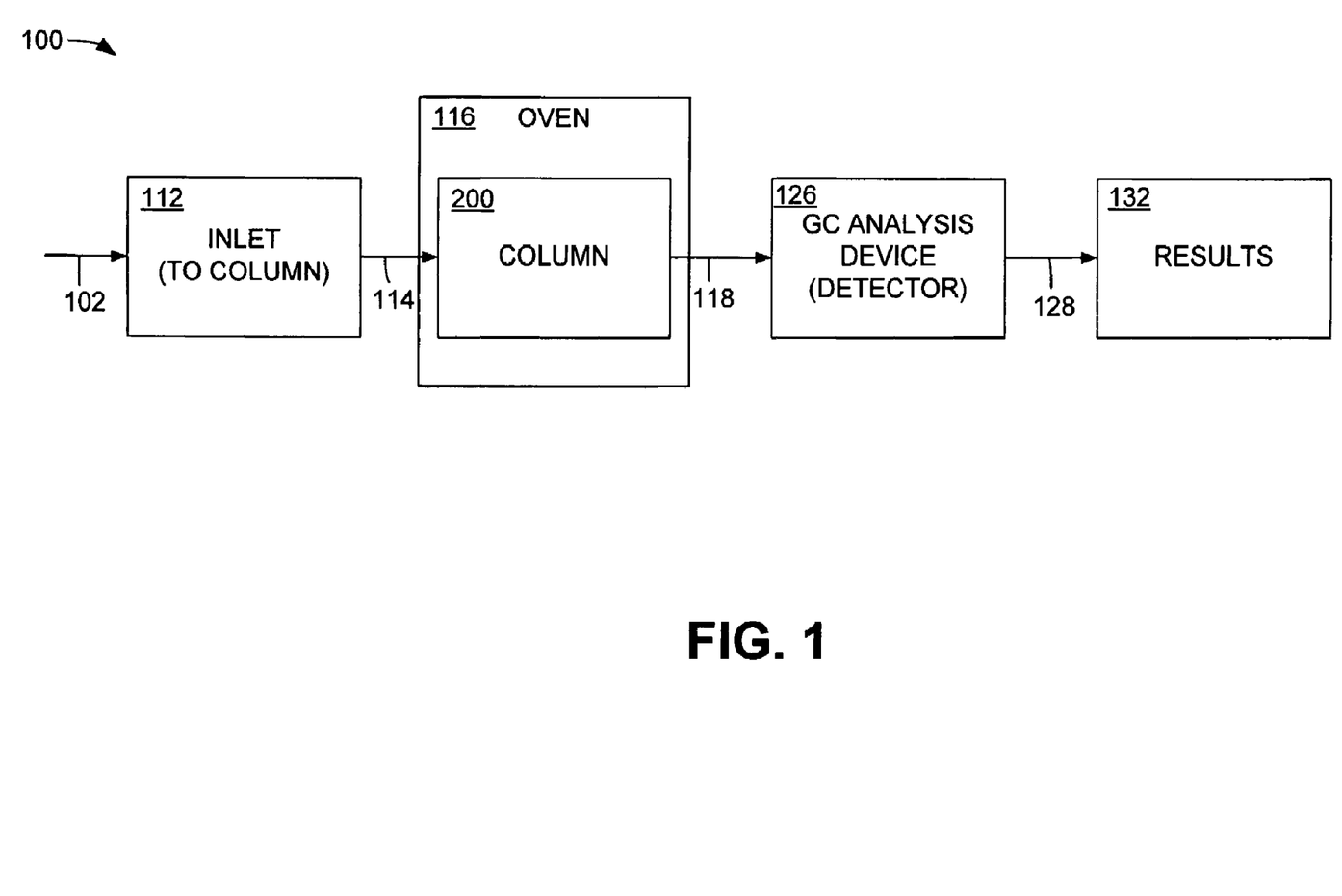
FIG. 1 is a schematic diagram illustrating a simplified chromatograph in which a chromatographic column constructed in accordance with an embodiment of the invention may operate.

FIG. 1 is a block diagram illustrating a simplified gas chromatograph 100, which is one possible device in which the analytical column of the invention may be implemented. The analytical column of the invention may also be used in any gas phase sampling device or in any analytical device, and may also be useful for liquid chromatography applications. The analytical column can be efficiently heated and cooled.

The gas chromatograph 100 includes an inlet 112, which receives a sample of material to be analyzed via connection 102 and provides the sample via connection 114 to, for example, an analytical column 200 constructed in accordance with an embodiment of the invention. In this example, the analytical column is a chromatographic column, and is also referred to as a capillary column, or just a column. To effectively separate compounds of interest during chromatography, the analytical column 200 may be heated to temperatures well above ambient temperature. The temperature to which the analytical column 200 is heated is dependent on the type of sample being analyzed and may vary during a sample run to analyze multiple compounds and elements from a single sample. Accordingly, the analytical column 200 is located in a temperature chamber, also referred to as an oven. In this example, the oven is a radiant oven 116 that provides radiant energy from a radiant energy source.

The output of the column 200 is connected via connection 118 to a detector 126 in the gas chromatograph 100. The output of the detector 126, via connection 128 is a signal representing the result 132 of the analysis.

Figure 2:
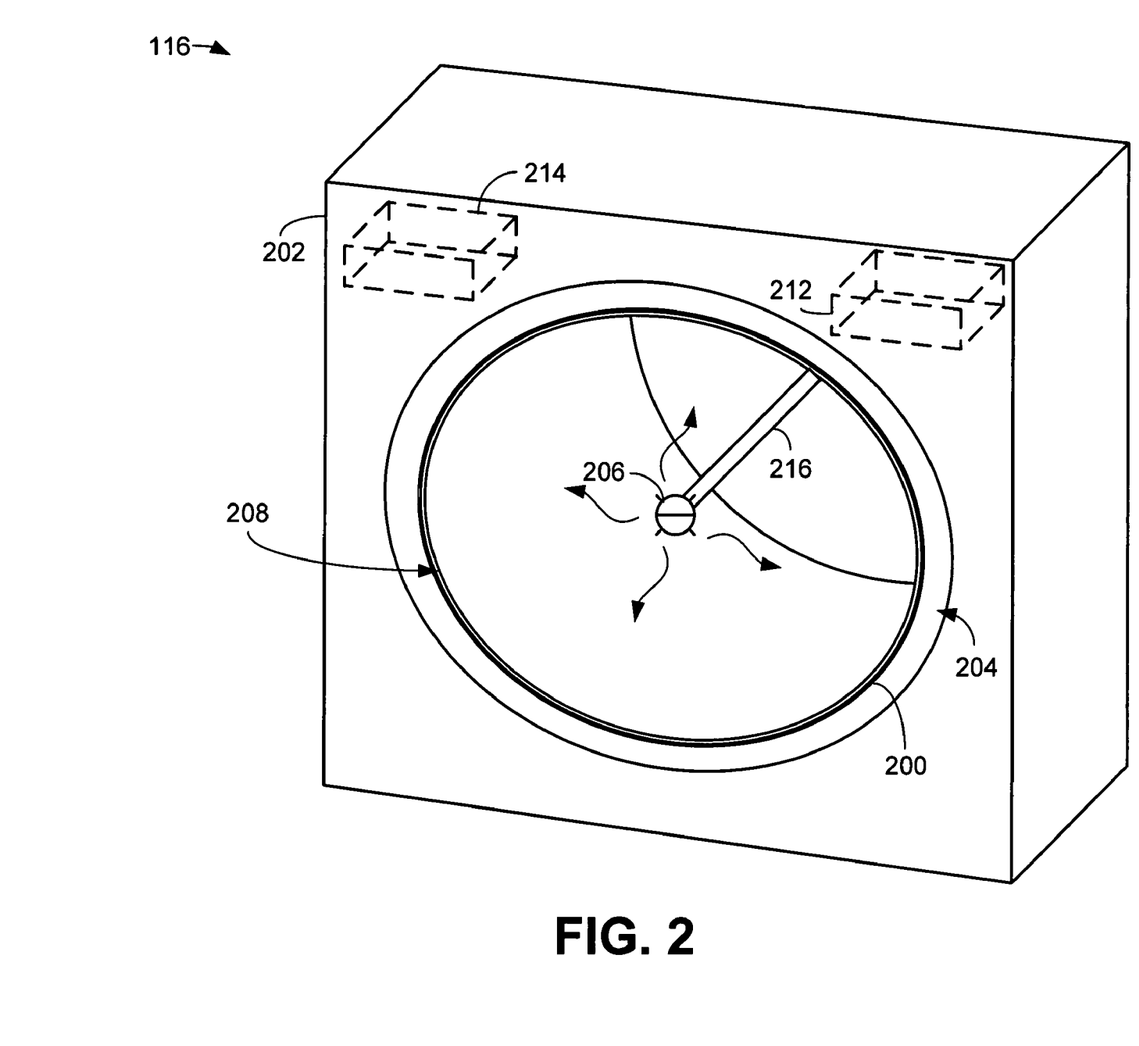
FIG. 2 is a schematic diagram illustrating a perspective view of an embodiment of the radiant oven and analytical column of FIG. 1.

FIG. 2 is a schematic diagram illustrating a perspective view of an embodiment of the radiant oven 116 and analytical column 200 of FIG. 1. The radiant oven 116 includes a housing 202 having a recess 204. The recess 204 is configured to releasably receive an analytical column 200. The analytical column 200, which in this example is a chromatographic column, is coiled and placed in the recess 204. In accordance with an embodiment of the invention, the analytical column 200 is coated with a material that efficiently absorbs radiant energy and converts the radiant energy to heat. The analytical column 200 will be described in detail below. The analytical column 200 can be either tightly or loosely coiled, depending on application. The input and output of the analytical column 200 is omitted for drawing clarity. A temperature sensor 208 can be secured to the analytical column 200 to precisely determine the temperature of the analytical column 200. In an embodiment, the temperature sensor 208 is coated with the same material with which the analytical column 200 is coated and placed in the radiant oven 116 at approximately the same distance from the heat source as the analytical column 200. In this way, the temperature sensor 208 is heated in the same manner as the analytical column 200.

The oven 116 also includes a radiant source 206 and control circuitry 212 configured to control the duty cycle of the power supplied to the radiant source. The control circuitry 212 uses information fed back from the temperature sensor 208 to determine the power required to achieve and maintain the temperature in the radiant oven 116 at a set point prescribed by the analysis. The duty cycle is the fraction of ON time of the radiant source relative to the total cycle (ON+OFF) time. In addition to controlling the duty cycle of the radiant source 206 it is often important to control the total cycle time as well. For example, a duty cycle of 20% can be achieved with an ON time of two minutes vs. a total time of ten minutes or an ON time of two seconds vs. a total time of ten seconds, etc. Although the duty cycle is the same, the total cycle times are quite different. The total cycle time (10 minutes, 10 seconds, 10 milliseconds, etc.) plays an important role for radiant sources having fast reaction times, such as a quartz halogen infrared (IR) radiant source. When the total cycle time is too long for a quartz halogen IR radiant source, the filament can cool significantly between cycles. Repeated heating and cooling of the filament in a quartz halogen IR radiant source causes fatigue and shortens the life of the filament. Many quartz halogen radiant source manufacturers suggest using "phase-angle fired" control where the total cycle time can be as small as a fraction of one cycle of the AC input power.

The radiant oven 116 optionally includes a fan 214, or other means for quickly cooling the oven 116. The radiant source 206 can be mounted on a pedestal 216. In one embodiment, the radiant source 206 is a quartz halogen IR bulb having a cylindrical profile. However, the shape of the radiant source 206 may differ. The radiant source can be an infrared (IR) source as mentioned above, a microwave source, an ultraviolet (UV) source, a visible (VIS) source, an X-ray source, or any other electromagnetic (EM) radiant source. In addition, the radiant source 206 may be one that emits radiant EM energy at multiple wavelengths, one that emits radiant EM energy at a single wavelength, such as a laser, and one that emits both visible and invisible IR, V, or any combination thereof. A cover is omitted from the radiant oven 116 for clarity.

The analytical column 200 is fabricated from fused silica glass, which is transparent to visible wavelengths of EM energy. Visible wavelengths of EM energy are desirable because they are high energy. Visible (VIS) light has a wavelength that ranges from approximately 400 nanometers (nm) to 700 nm. Infrared (IR) radiation ranges in wavelength from approximately $0.01-7\times10^{-5}$ centimeters; and ultraviolet (UV) radiation ranges in wavelength from approximately $4\times10^{-5}-10^{-7}$ centimeters. In accordance with an embodiment of the invention, and as will be described in detail below, the analytical column 200 is coated with a material that exhibits a high solar absorbance at the wavelength or wavelengths of the output of the radiant source 206 including the desirable visible region. In an embodiment, the analytical column 200 is coated with a material that exhibits a high solar absorbance at ultraviolet (UV) and visible (VIS) wavelengths and converts the radiant energy into heat. Solar absorptivity, denoted $\alpha$, is the fraction of incoming light that is absorbed by the material and consequently converted to heat. Solar absorptivity is not only material-dependent but also dependent on wavelength ($\lambda$) and incidence angle ($\theta$) of the incident light (i.e., $\alpha=\alpha_{\lambda,\theta}$). However, for practicality and often as a good approximation, $\alpha$ is most often quoted as a single value representing an average over all wavelengths (or a subset of wavelengths, such as the wavelengths of V, VIS, or IR) and incidence angles. Values generally range from 0 to 1 with a high value generally of 0.85 or greater. The coating on the analytical column 200 converts the radiant EM energy to heat. The heat is transmitted via conduction directly to the analytical column 200.

Figure 3:
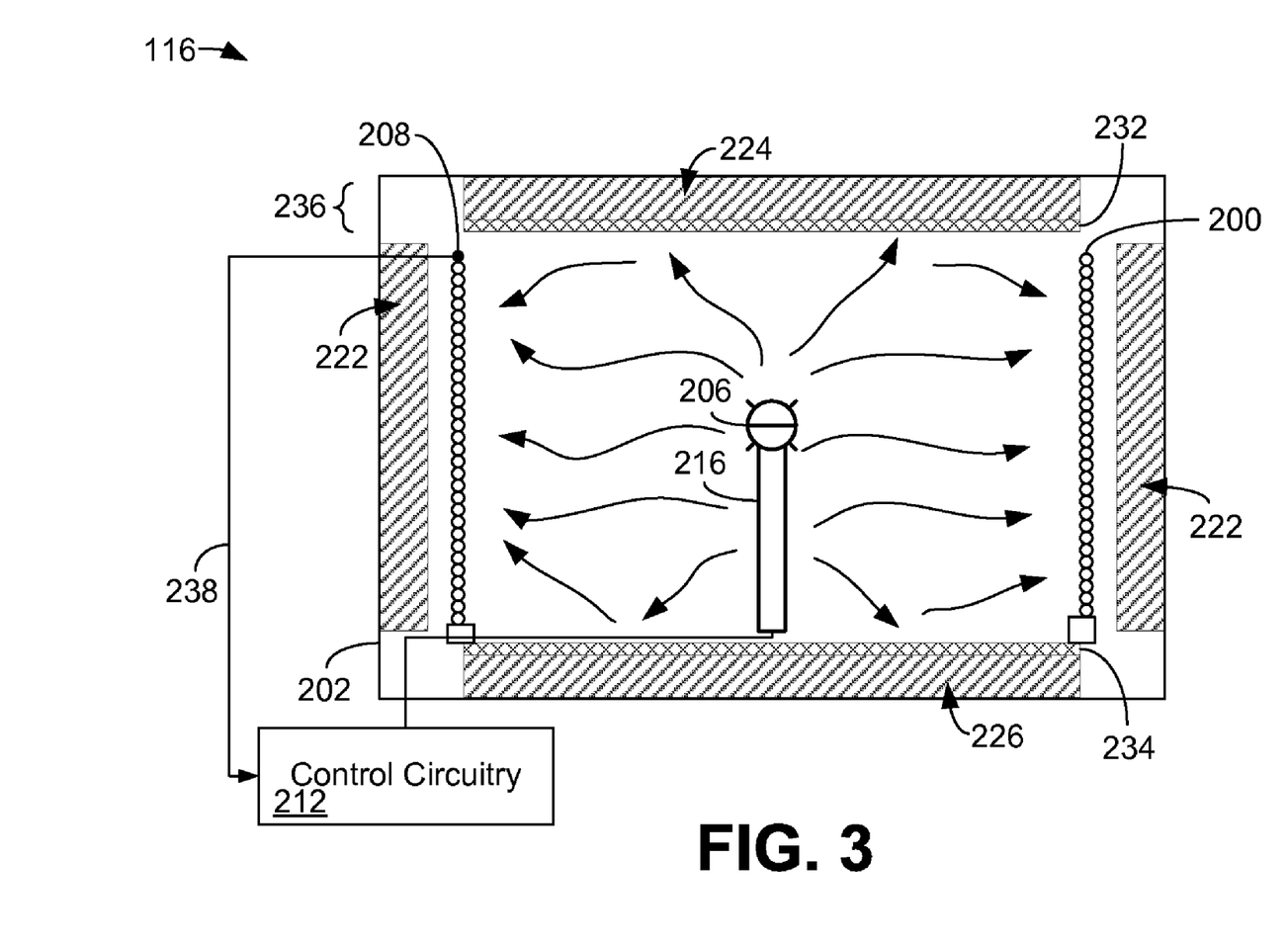
FIG. 3 is a schematic diagram illustrating a cross-sectional view of the radiant oven of FIG. 2 including the analytical column.

FIG. 3 is a schematic diagram illustrating a cross-sectional view of the radiant oven 116 of FIG. 2 including the analytical column. The radiant oven 116 includes a housing 202 in which the analytical column 200 is located. The housing 202 also includes the radiant source 206 and pedestal 216. In FIG. 3, the control circuitry 212 is depicted as a separate element, but in practice would likely be integrated within the housing 202.

As shown in FIG. 3, an analytical column 200 is tightly coiled inside the oven 116. The temperature sensor 208 is secured, for example by a releasable bonding technique, to the outer surface of the analytical column 200. The radiant oven 116 also includes an upper reflector 232 and a lower reflector 234. The upper reflector 232 and the lower reflector 234 reflect radiant EM energy back towards the radiant source 206 to conserve energy by not heating the oven walls. The upper reflector 232 and the lower reflector 234 are preferably fabricated from a material that is reflective at the wavelengths of the output of the radiant source 206. A material's reflectivity, denoted $\rho$, is the fraction of incoming light that is reflected off of the material's surface. Like $\alpha$, $\rho$ is dependent on both wavelength and incidence angle and is often quoted as an average over a subset of wavelengths and incidence angles. Typical reflectors for UV, VIS, and IR are metals—particularly aluminum, silver, and gold. Gold is useful for reflecting IR energy and has the added property that it is resistant to oxidation making its optical properties stable over time. Aluminum is slightly better than gold in the VIS region, but must be coated to prevent oxidation. The useful range of aluminum can be further increased into the UV region by adding an enhancing over-coating (e.g., $MgF_2$). Another class of materials useful for UV/VIS/IR reflectance is dielectrics. Dielectrics are often used as reflectors for lasers as they can be tuned to have peak reflectivity over a narrow range of wavelengths. The radiant oven 116 also includes insulation portions 222, 224 and 226 to maintain the interior of the oven 116 at the desired temperature. In this embodiment, the insulation 224 and the upper reflector 232 form a cover 236.

The temperature sensor 208 precisely determines the temperature of the analytical column 200. A feedback signal provided from the temperature sensor 208 via connection 238 to the control circuitry 212 can be used to control the duty cycle at which the radiant source operates, and thereby precisely control the temperature in the radiant oven 116.

Positioning the analytical column 200 vertically in the oven 116 minimizes radiant energy gradients due to natural convection when the diameter of the coiled analytical column 200 is larger than the height. Positioning the analytical column 200 so that the smaller of the diameter or the height in the direction of the plane of gravity minimizes the effects of natural convection. Alternatively, the radiant source 206 may be controlled, or modified, to minimize the effects of natural convection. In another embodiment, the analytical column 200 may be positioned horizontally if the height is larger than the diameter.

Figure 4A:
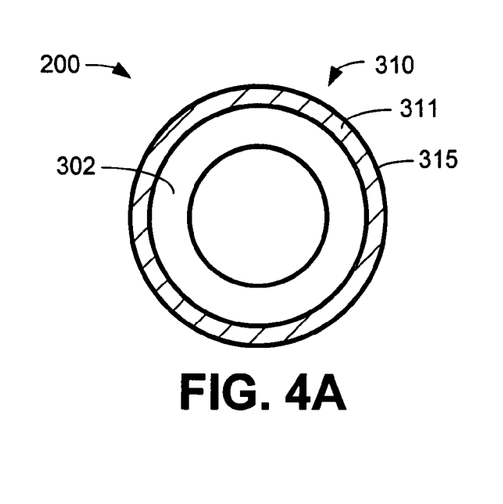
FIGS. 4A, 4B and 4C are schematic diagrams collectively illustrating cross-sectional and side views of embodiments of the analytical column of FIGS. 2 and 3.
Figure 4B:
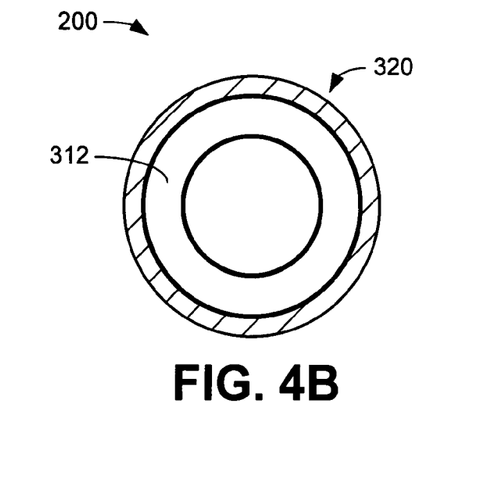

FIGS. 4A and 4B are schematic diagrams collectively illustrating cross-sectional and side views of an embodiment of the analytical column of FIGS. 2 and 3. FIG. 4A is a cross-sectional view of the analytical column 200. The analytical column 200 comprises a wall 302 that defines an inner diameter of the analytical column 200 and a coating 310. The wall is typically fabricated from fused silica, or a similar material. The coating is a material that exhibits a high solar absorbance, referred to as $\alpha$, at the wavelength of the output of the radiant source 206. In an embodiment, the coating 310 is formed from a material, such as polyimide, into which a material that exhibits high solar absorbance has been added. For example, the coating 310 can be one or more layers of polyimide including carbon black. In this embodiment, the polyimide is absorbent of the IR energy and the carbon black enhances the absorption of the visible (VIS) light, which is higher in energy than the IR light. The combination of the polyimide and the carbon black absorb the IR and the VIS energy emitted by the radiant source 206 (FIGS. 2 and 3) and efficiently convert the radiant energy to heat.

In an embodiment, a fused silica column having an inner diameter (ID) of 320 micrometers ($\mu$m) and an outer diameter (OD) of 445 $\mu$m is coated with a base coating 311 of several layers of polyimide totaling approximately 18-20 $\mu$m thick. Then a final coating 315 of polyimide impregnated with approximately 1-2% carbon black approximately 4-5 $\mu$m thick is applied over the polyimide. The final coating 315 of polyimide and carbon black absorbs the UV or VIS light, converts the UV or VIS light to heat and efficiently transfers the heat to the wall 302 of the analytical column 200.

In another embodiment, a significantly thicker initial coating of polyimide, approximately 35 to 40 $\mu$m thick, is applied to the wall 302 of the analytical column 200. At sufficient thickness, the relatively thick coating of polyimide will become opaque to visible light and will efficiently convert the radiant energy to heat without the carbon black polyimide layer.

FIG. 4B shows another embodiment in which the analytical column 200 is coated with anodized aluminum. In FIG. 4B, the coating 320 is aluminum, which is then anodized to form a black, or dark, surface. When coated with anodized aluminum, the operating temperature of the analytical column can range up to, for example, 450 degrees Celsius, or greater. Further, the aluminum coating protects the silica glass material of the wall 312. The dark surface absorbs the radiant EM energy emitted from the radiant source 206 and converts the radiant EM energy to heat. The heat is transmitted directly to the wall 302 of the analytical column 200 via conduction.

Figure 4C:
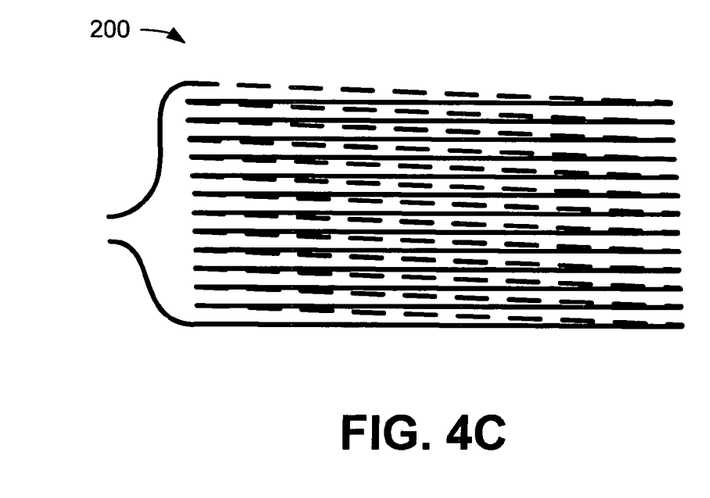

FIG. 4C is a schematic side view of the analytical column 200 of FIG. 4A or 4B. The analytical column 200 is tightly coiled so that temperature fluctuations between subsequent coils are minimized and so that the coils may insulate each other.

Figure 5:
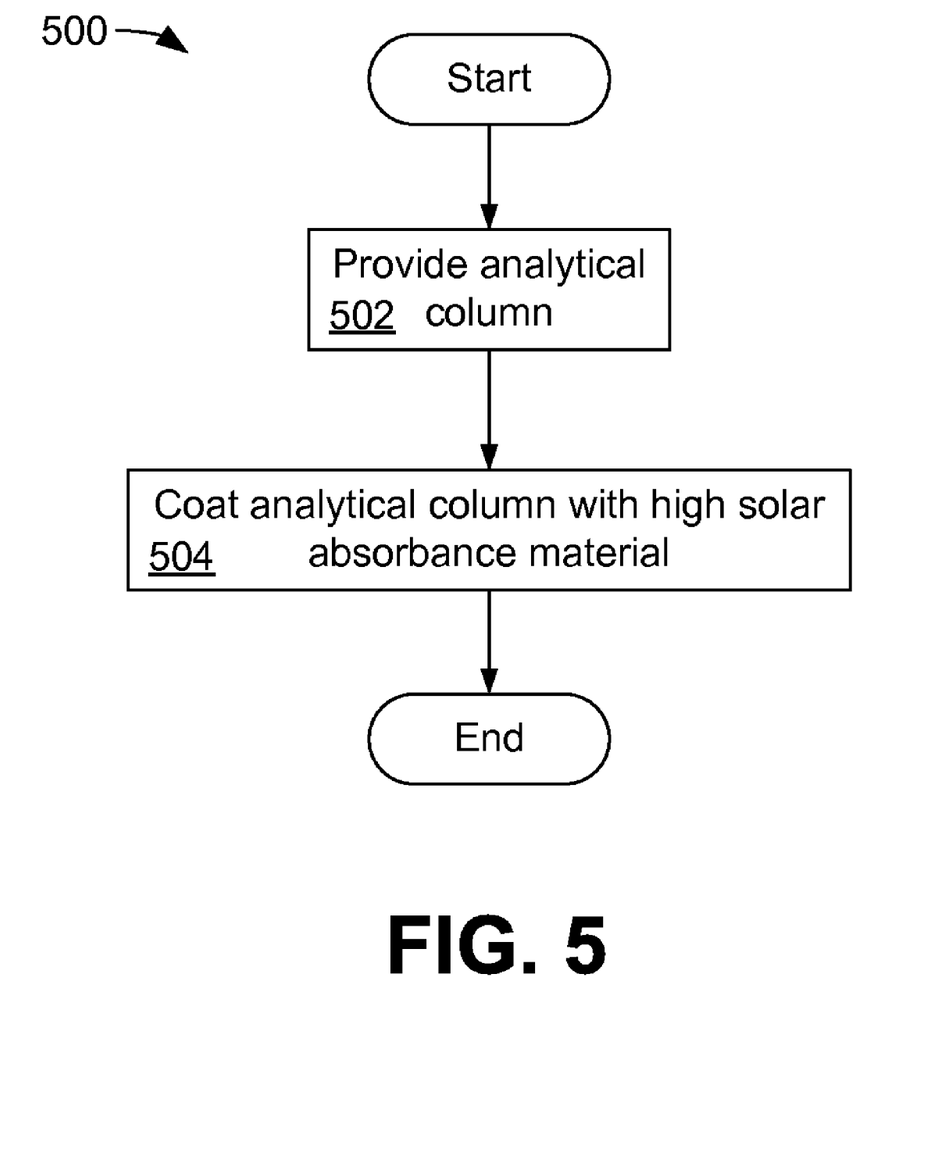
FIG. 5 is a flowchart illustrating a method for constructing an analytical column in accordance with an embodiment of the invention.

FIG. 5 is a flowchart illustrating a method for constructing an analytical column in accordance with an embodiment of the invention. In block 502 an analytical column is provided. In block 504, the analytical column is coated with a material that exhibits a high solar absorbance, $\alpha$, at the wavelengths of the output of the radiant source 206. In an embodiment, the analytical column 200 is coated with polyimide that includes carbon black. The coating can be applied to the analytical column via, for example, an extruding process in which the uncoated analytical column is drawn through a liquid polyimide including the carbon black material. The coating is then cured to form a solid coating over the analytical column. In another embodiment, the coating can be aluminum, which is then anodized to form a black, or dark, surface.

Figure 6:
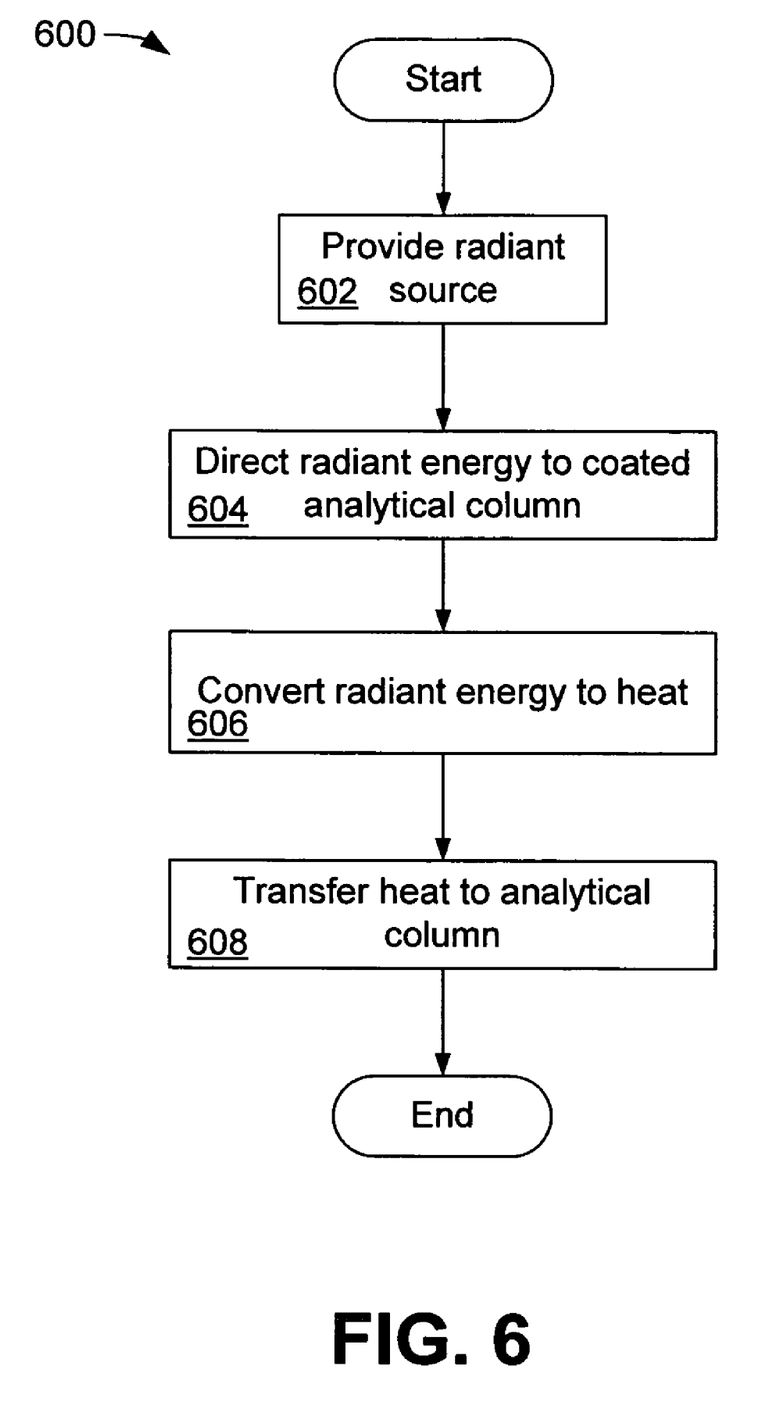
FIG. 6 is a flowchart illustrating a method for efficiently heating an analytical column.

FIG. 6 is a flowchart 600 illustrating a method for efficiently heating an analytical column. The blocks in the flowchart illustrate the operation of one embodiment of the invention and can be executed in the order shown, out of the order shown or in parallel. In block 602 a radiant source is provided. In block 604 the output of the radiant source is directed to the analytical column 200. In block, 606, the coating 310 of the analytical column 200 converts the radiant energy to heat. In block 608, heat is transferred from the coating 310 to the wall 302 of the analytical column 200 to efficiently and evenly heat the column.

The foregoing detailed description has been given for understanding exemplary implementations of the invention and no unnecessary limitations should be understood therefrom as modifications will be obvious to those skilled in the art without departing from the scope of the appended claims and their equivalents.

What is claimed is:

1. An analytical column having a coating, the coating comprising polyimide and no more than approximately 1-2% carbon black in which the coating absorbs at least one of ultraviolet (UV) and visible (VIS) radiant energy and converts the radiant energy into heat.

2. The analytical column of claim 1, in which the coating has a solar absorbance factor of approximately greater than 0.85 for UV or VIS wavelengths.

3. The analytical column of claim 1, in which the coating absorbs visible light.

4. The analytical column of claim 1, in which the coating absorbs UV light.

5. The analytical column of claim 1, in which the coating is in direct contact with the analytical column.

6. The analytical column of claim 1, further comprising a temperature sensor in contact with the analytical column.

7. A chromatograph, comprising:
   an inlet coupled to a chromatographic column having a coating, the coating comprising polyimide and no more than approximately 1-2% carbon black, in which the coating absorbs at least one of ultraviolet (UV) and visible (VIS) radiant energy and converts the radiant energy into heat;
   an oven having a source that provides the radiant energy; and
   a detector for providing chromatographic results.

8. The chromatograph of claim 7, in which the coating has a solar absorbance factor of approximately greater than 0.85 for UV or VIS wavelengths.

9. The chromatograph of claim 7, in which the coating absorbs visible light.

10. The chromatograph of claim 7, in which the coating is in direct contact with the analytical column.

11. The chromatograph of claim 7, further comprising a temperature sensor in contact with the analytical column.

12. A method for making an analytical column, comprising:

providing an analytical column;

coating the analytical column with polyimide including no more than approximately 1-2% carbon black such that the column absorbs at least one of ultraviolet (UV) and visible (VIS) radiant energy and that converts the radiant energy into heat.

13. The method of claim 12, in which the coating has a solar absorbance factor of approximately greater than 0.85 for UV and VIS wavelengths.

14. The method of claim 12, in which the coating absorbs visible light.

* * * * *